United States Patent
Jeon et al.

(10) Patent No.: US 10,316,297 B2
(45) Date of Patent: Jun. 11, 2019

(54) FEEDBACK-RESISTANT ACETOHYDROXY ACID SYNTHASE VARIANT AND METHOD FOR PRODUCING L-VALINE USING THE SAME

(71) Applicant: CJ CHEILJEDANG CORPORATION, Seoul (KR)

(72) Inventors: Ae Ji Jeon, Seoul (KR); Byeong Cheol Song, Yongin-si (KR); Jong Hyun Kim, Anyang-si (KR); Hye Won Kim, Seongnam-si (KR); Ji Hye Lee, Anyang-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 15/501,645

(22) PCT Filed: Aug. 5, 2015

(86) PCT No.: PCT/KR2015/008184
§ 371 (c)(1),
(2) Date: Feb. 3, 2017

(87) PCT Pub. No.: WO2016/021932
PCT Pub. Date: Feb. 11, 2016

(65) Prior Publication Data
US 2017/0226488 A1    Aug. 10, 2017

(30) Foreign Application Priority Data

Aug. 5, 2014    (KR) .................. 10-2014-0100669

(51) Int. Cl.
*C12P 13/08*    (2006.01)
*C12N 9/10*    (2006.01)
*C12N 9/88*    (2006.01)
*C12R 1/15*    (2006.01)

(52) U.S. Cl.
CPC ............. *C12N 9/1022* (2013.01); *C12N 9/88* (2013.01); *C12P 13/08* (2013.01); *C12R 1/15* (2013.01); *C12Y 202/01006* (2013.01)

(58) Field of Classification Search
None
See application file for complete search history.

(56) References Cited

U.S. PATENT DOCUMENTS

| | | | | |
|---|---|---|---|---|
| 7,323,321 B2 * | 1/2008 | Rayapati | .................. | C12N 9/88 435/106 |
| 7,332,310 B2 * | 2/2008 | Nakagawa | ............. | C07K 14/34 435/115 |
| 7,635,579 B2 * | 12/2009 | Rayapati | .................. | C12N 9/88 435/106 |

FOREIGN PATENT DOCUMENTS

| | | |
|---|---|---|
| KR | 10-2006-0024437 A | 3/2006 |
| KR | 10-2008-0025355 A | 3/2008 |
| KR | 10-1117022 B1 | 3/2012 |

OTHER PUBLICATIONS

NCBI Reference Sequence: WP_003861429.1 (Oct. 1, 2015).

* cited by examiner

*Primary Examiner* — Hope A Robinson
(74) *Attorney, Agent, or Firm* — Seed IP Law Group LLP

(57) ABSTRACT

The present disclosure relates to an acetohydroxy acid synthase variant in which the feedback inhibition to L-valine is released, a polynucleotide encoding the acetohydroxy acid synthase variant, an expression vector including the polynucleotide, a microorganism producing L-valine including the acetohydroxy acid synthase variant, and a method for producing L-valine using the microorganism.

2 Claims, No Drawings
Specification includes a Sequence Listing.

FEEDBACK-RESISTANT ACETOHYDROXY ACID SYNTHASE VARIANT AND METHOD FOR PRODUCING L-VALINE USING THE SAME

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_429USPC_SEQUENCE_LISTING.txt. The text file is 4.5 KB, was created on Jan. 30, 2017, and is being submitted electronically via EFS-Web.

TECHNICAL FIELD

The present disclosure relates to an acetohydroxy acid synthase variant in which the feedback inhibition to L-valine is released, a polynucleotide encoding the acetohydroxy acid synthase variant, an expression vector including the polynucleotide, a microorganism producing L-valine including the acetohydroxy acid synthase variant, and a method for producing L-valine using the microorganism.

BACKGROUND ART

L-valine is an essential amino acid and effectively used as a material for feed components and foods.

Since branched-chain amino acids (e.g., L-valine, L-isoleucine, and L-leucine) are biosynthesized using the same enzyme it is known that it is difficult to prepare a single kind of branched amino acid on a large industrial scale via fermentation. Additionally, the biosynthesis also has a problem in that a feedback inhibition occurs on the major enzymes by the final product (i.e., L-valine) or a derivative thereof and thus there is a limitation with respect to the fermentation.

DISCLOSURE

Technical Problem

Under the circumstances, the present inventors have made efforts to develop an effective method for producing L-valine. As a result, they have verified a novel acetohydroxy acid synthase variant in which the feedback inhibition by L-valine is released, and confirmed that a microorganism producing L-valine including the variant has an excellent ability to produce L-valine compared to the parent strain not containing the variant, thereby completing the present disclosure.

Technical Solution

An object of the present disclosure is to provide an acetohydroxy acid synthase variant in which the feedback inhibition to L-valine is released.

Another object of the present disclosure is to provide a polynucleotide encoding the acetohydroxy acid synthase variant and an expression vector containing the polynucleotide.

A further object of the present disclosure is to provide a microorganism producing L-valine, including the acetohydroxy acid synthase variant A still further object of the present disclosure is to provide a method for producing L-valine using the microorganism producing L-valine.

Advantageous Effects of the Invention

The acetohydroxy acid synthase variant according to the present disclosure is in a state where the feedback inhibition to L-valine is released. Therefore, a microorganism for producing L-valine, including the variant, can produce L-valine in high yield compared to the parent strain.

BEST MODE

In an aspect, the present disclosure provides an acetohydroxy acid synthase variant in which the $137^{th}$ amino acid from the N-terminus of an amino acid sequence of SEQ ID NO: 3, leucine (L), is substituted with an amino acid other than leucine, and thus the feedback inhibition to L-valine is released.

As used herein, the term "L-valine" refers to an L-amino acid having a chemical formula of $(CH_3)_2CHCH(NH_2)COOH$, which is one of the essential amino acids and structurally belongs to the branched-chain amino acids, together with L-leucine and L-isoleucine.

As used herein, the term "acetohydroxy acid synthase" refers to the first enzyme in the L-valine biosynthesis and is also called acetolactate synthase. Acetohydroxy acid synthase catalyzes decarboyxlation of pyruvate and a condensation reaction with another pyruvate molecule to produce acetolactate, which is a precursor of valine, or catalyzes decarboyxlation of pyruvate and a condensation reaction with 2-ketobutyrate to produce acetohydroxybutyrate, which is a precursor of isoleucine.

Acetohydroxy acid synthase is encoded by two genes, i.e., ilvB and ilvN. The ilvB gene encodes the large subunit of acetohydroxy acid synthase and the ilvN gene encodes the small subunit of acetohydroxy acid synthase, respectively. Between them, the small subunit encoded by the ilvN gene is thought to be importantly involved in the feedback inhibition.

The acetohydroxy acid synthase encoded by the ilvN gene may have an amino acid sequence of SEQ ID NO: 3, but is not particularly limited thereto.

As used herein, the term "feedback inhibition" refers to the inhibition of a reaction at the early state of an enzyme system by a final product in the enzyme system. For the purpose of the present disclosure, the feedback inhibition refers to the inhibition of the activity of acetohydroxy acid synthase, which mediates the first step of L-valine biosynthesis, by L-valine, but is not limited thereto. Accordingly, in a case when the feedback inhibition of acetohydroxy acid synthase is released, it can improve the productivity of L-valine. In the present disclosure, it was confirmed that when the $137^{th}$ amino acid from the N-terminus of an amino acid sequence of SEQ ID NO: 3, leucine, is substituted with a different amino acid, specifically phenylalanine, Phe, F), the feedback inhibition to L-valine was released.

The acetohydroxy acid synthase, in which the feedback inhibition to L-valine is released, may specifically have an amino acid sequence of SEQ ID NO: 4.

Additionally, the acetohydroxy acid synthase variant in which the feedback inhibition to L-valine is released includes, without limitation, not only the variant having the amino acid sequence of SEQ ID NO: 4 but also the variants having a homology of 80% or higher, specifically 90% or higher, more specifically 95% or higher, and even more specifically 99%, to the amino acid sequence of SEQ ID NO: 4, wherein the feedback inhibition to L-valine is actually released compared to that of the wild-type acetohydroxy acid synthase. It is obvious that any amino acid sequence having a biological activity substantially the same as or corresponding to the protein having the amino acid sequence of SEQ ID NO: 4 should also belong to the scope of the present disclosure, although the amino acid sequence may have deletion, modification, substitution, or addition in part of the sequence.

As used herein, the term "homology" refers to a percentage of identity between two polynucleotides or polypeptide moieties. The homology between sequences from a moiety to another moiety may be determined by the technology known in the art. For example, the homology may be determined by directly arranging the sequence information of two polynucleotide molecules or two polypeptide molecules using an easily accessible computer program. Examples of the computer program may include BLAST (NCBI), CLC Main Workbench (CLC bio), MegAlign™ (DNASTAR Inc.), etc. Additionally, the homology between polynucleotides may be determined by hybridizing polynucleotides under the condition of forming a stable double-strand between the homologous regions, disassembling with a single strand-specific nuclease, followed by size determination of the disassembled fragments, As used herein, the term "homologous" refers to a correlation between proteins where all grammatical forms and spelling variations include superfamily-derived proteins and other species-derived homologous proteins having a "common evolutionary origin". Such proteins (and coding genes thereof) have a sequence homology reflected by a high degree of sequence similarity. However, in general use and in the present disclosure, when the term "homology" is modified by an adjective such as "very high", it refers to a sequence similarity, but not a common evolutionary origin.

According to a specific embodiment of the present disclosure, the acetohydroxy acid synthase variant in which the feedback inhibition is released may be one generated by a mutation of an L-valine-producing microorganism. The mutation of the microorganism may be performed by various methods well-known in the art, and any one from the physical or chemical mutagenesis may be used. For example, the chemical mutagenic factor suitable for the present disclosure may include N-methyl-N'-nitro-N-nitrosoguanidine (NTG), diepoxybutane, ethyl methane sulfonate, mustard compounds, hydrazine, and nitrous acid, but is not limited thereto. In addition, examples of the chemical mutagenic factor may include N-methyl-N'-nitro-N-nitrosoguanidine (NTG), diepoxybutane, ethyl methane sulfonate, mustard compounds, hydrazine, and nitrous acid, but are not limited these compounds. Additionally, examples of the physical mutagenic factor may include ultraviolet and gamma radiation, but are not limited thereto.

Additionally, in a specific embodiment of the present disclosure, *Corynebacterium glutamicum* KCCM11201P (Korean Patent No. 10-1117022) was used as a parent strain for obtaining a modified strain of a microorganism with improved ability of producing L-valine. The strain is a modified strain having a resistance to α-aminobutyric acid (ABA), α-hydroxyvaline (ARV), thiazole alanine (TA), and norvaline (NV), In the present disclosure, the *Corynebacterium glutamicum* KCCM11201P was treated with NTG, and among the strains, the strain showing a resistance to α-aminobutyric acid (ABA) was obtained and named as "NA 100-311". The "NA100-311" strain showed an increase of about 20.3% in the amount of L-valine production as compared to that produced by an equal amount of cells of the parent strain. Additionally, upon analysis of the nucleotide sequence, it was confirmed that a mutation occurred on the amino acid sequence of the modified strain of acetohydroxy acid synthase, and specifically, the $137^{th}$ amino acid on the amino acid sequence of SEQ ID NO: 3, i.e., leucine, was substituted with phenylalanine (Example 2).

In another aspect, the present disclosure provides a polynucleotide encoding the acetohydroxy acid synthase variant and an expression vector including the polynucleotide.

The acetohydroxy acid synthase and the variant are the same as explained above.

As used herein, the term "polynucleotide" refers to a polymer of nucleotides chain-extended lengthwise by a covalent bond of nucleotide units, and in general a DNA or RNA strand with a certain length. In the present disclosure, it refers to a polynucleotide encoding the acetohydroxy acid synthase variant.

For example, the polynucleotide encoding the acetohydroxy acid synthase variant may have a nucleotide sequence of SEQ ID NO: 5, which is a polynucleotide sequence encoding the acetohydroxy acid synthase of SEQ ID NO: 3, where the $409^{th}$ nucleotide, i.e., C, was substituted with T, but is not limited thereto.

As used herein, the term "vector" refers to any carrier for cloning and/or transferring nucleotides into a host cell. A vector may be a replicon to allow for the replication of a fragment(s) combined with other DNA fragment(s). "Replicon" refers to any genetic unit acting as a self-replicating unit for DNA replication in vivo, that is, replicable by self-regulation (e.g., plasmid, phage, cosmid, chromosome, and virus). In the present disclosure, the vector is not particularly limited but any vector known in the art can be used as long as it can replicate in a host. The vector used in the preparation of the recombinant vector may be plasmids, cosmids, viruses, and bacteriophages in a natural state or in a recombinant state, For example, as a phage vector or cosmid vector, pWE15, M13, λEMBL3, λEMBL4, λFIXII, λDASHII, λZAPII, λgt10, λgt11, Charon4A, Charon21A, etc., may be used, and as a plasmid vector, those based on pDZ vector, pBR, pUC, pBluescriptII, pGEM, pTZ, pCL, pET, etc., may be used. The vectors that can be used in the present disclosure are not particularly limited but any known expression vector may be used. Specifically, pDZ (Korean Patent Application Publication No. 2008-0025355 is incorporated in its entirety as a reference in the present disclosure) may he used, but is not limited thereto.

In still another aspect, the present disclosure provides a microorganism producing L-valine, including the acetohydroxy acid synthase variant.

The L-valine, acetohydroxy acid synthase, and variant are the same as explained above.

As used herein, the term, "a microorganism producing L-valine" refers to a prokaryotic or eukaryotic microorganism strain capable of producing L-valine within a bioorganism. For the purpose of the present disclosure, both a prokaryotic cell and a eukaryotic cell may be possible as long as the microorganism can produce L-valine, for example, a microorganism strain of the genus Corynebacterium may be included (e.g., *Corynebacterium glutamicum*)

The microorganism producing L-valine including the acetohydroxy acid synthase variant may include both a microorganism, which includes the sequence of an acetohydroxy acid synthase variant due to the mutation of a gene encoding the acetohydroxy acid synthase on the chromosome, and/or a microorganism, which includes the acetohydroxy acid synthase variant due to the introduction of a vector including a polynucleotide encoding the acetohydroxy acid synthase variant, but is not limited thereto.

Additionally, the microorganism producing L-valine including the acetohydroxy acid synthase variant may be a microorganism in which the acetohydroxy acid synthase variant activity is enhanced compared to that of the parent strain.

Examples of the methods for enhancing the activity of the acetohydroxy acid synthase variant may include a method of increasing the intracellular copy number of a gene encoding the variant, a method of introducing a modification in the control sequence of a gene encoding the variant on the chromosome, a method of substituting the control sequence of a gene encoding the variant on the chromosome with a sequence having strong activity, a method of substituting the gene encoding the variant on the chromosome with a mutated gene to increase the activity of the variant, and a method of introducing a modification in the gene encoding the variant protein on the chromosome to enhance the activity of the variant, but are not limited thereto.

As used herein, the term "introduction" refers to a method for delivering a polynucleotide encoding the acetohydroxy acid synthase variant or a vector including the polynucleotide into a host cell. The introduction can be easily performed according to a conventional method in the art. In general, a $CaCl_2$ precipitation method, a Hanahan method with improved efficiency using dimethyl sulfoxide (DMSO) as a reducing agent in the $CaCl_2$ precipitation method, electroporation, a $CaPO_4$ precipitation method, a protoplast fusion method, a stirring method using silicon carbide fiber, a transformation using PEG dextran sulfate-, lipofectamine-, and dry/suppression-mediated transformations, etc. The method for transforming the vector may not be limited to these methods, but any method for transformation or transfection commonly used in the art may be used without limitation. Additionally, the delivered polynucleotide may be inserted into the chromosome of a host cell and located therein or outside the chromosome, as long as the polynucleotide can be expressed in the host cell. Additionally, the polynucleotide may be introduced in any form, as long as the polynucleotide can be introduced into a host cell and expressed therein. For example, the polynucleotide may be introduced into a host cell in the form of an expression cassette, which is a polynucleotide construct including all essential elements required for self-expression, but is not limited thereto. The expression cassette may conventionally include a promoter operably connected to the open reading frame (hereinafter, "ORF") of the gene, a transcription termination signal, a ribosome-binding domain, and a translation termination signal. The expression cassette may be in the form of an expression vector capable of self-replication. Additionally, the polynucleotide may be introduced into a host cell as it is and operably connected to a sequence necessary for its expression in a host cell, but is not particularly limited thereto.

In a specific embodiment of the present disclosure, the parent strain of *Corynebacterium glutamicum* KCCM11201P was transformed with a vector including a nucleotide sequence encoding an a.cetohydroxy acid synthase variant and the ability to produce L-valine was analyzed, and as a result, the transformed strain was shown to have an increased ability to produce L-valine compared to that of the parent strain.

In still another aspect, the present disclosure provides a method for producing L-valine using a microorganism of the genus *Corynebacterium* producing L-valine.

The L-valine, acetohydroxy acid synthase, variant, and microorganism are the same as explained above.

In the present disclosure, the method for culturing the strain producing L-valine for the production of L-valine may be performed using a method for culturing a microorganism of the genus *Corynebacterium* which is well known in the art. Specifically, examples of the culturing methods may include batch culture, continuous culture, and fed-batch culture, but are not limited thereto. These various methods are disclosed in, for example, "Biochemical Engineering" (James M. Lee, Prentice-Hall International Editions, pp 138-176, 1991), etc.

The medium used for the culture must meet the requirements for the culture of a specific strain. The culture medium for a microorganism of the genus Corynebacterium is disclosed (e.g., *Manual of Methods for General Bacteriology*. American Society for Bacteriology. Washington D.C., USA. 1981), Examples of the carbon sources to be used in the medium may include sugars and carbohydrates such as glucose, saccharose, lactose, fructose, maltose, starch, and cellulose; oils and fats such as soybean oil, sunflower oil, castor oil, and coconut fat; fatty acids such as palmitic acid, stearic acid, and linolic acid; alcohols such as glycerol and ethanol; and organic acids such as acetic acid. These carbon sources may be used alone or in combination but are not limited thereto. Examples of the nitrogen sources to be used in the medium may include peptone, yeast extract, meat gravy, malt extract, corn steep liquor, and soybean flour; and inorganic nitrogen sources such as urea, ammonium sulfate, ammonium chloride, ammonium phosphate, ammonium carbonate, and ammonium nitrate. These nitrogen sources may also be used alone or in combination, but are not limited thereto. Examples of the phosphorus sources to be used in the medium may include potassium dihydrogen phosphate or dipotassium hydrogen phosphate or the corresponding sodium-containing salts. Additionally, the culture medium must include metal salts such as magnesium sulfate and iron sulfate that are necessary for growth. In addition to the above substances, essential materials for growth, such as amino acids and vitamins, may also be included.

Additionally, precursors suitable for a culture medium may be used. These sources may be added to a culture in an appropriate manner during the culture by a batch culture or a continuous culture, but the methods are not limited thereto.

Additionally, the pH of a culture may be adjusted during the culture by adding a basic compound such as sodium hydroxide, potassium hydroxide, and ammonia, or an acidic compound such as phosphoric acid and sulfuric acid to the culture in an appropriate manner. During the culture, an antifoaming agent, such as fatty acid polyglycol ester, may be added to prevent foam generation. Additionally, oxygen or an oxygen-containing gas may be injected into the culture in order to maintain an aerobic state of the culture. Generally, the culture temperature may be in the range from 20° C. to 45° C., but is not limited thereto. The culture may be continued until the amount of L-valine production reaches the maximum level, and normally for from 10 hours to 160 hours, but is not limited thereto. L-valine may be released into the culture medium or may be included in the cells.

The method of preparing L-valine of the present disclosure may further include recovering the L-valine from a cultured microorganism or the cultured medium. The methods for recovering an L-amino acid front a cultured microorganism or a culture may include those well-known in the art such as centrifugation, filtration, anion exchange chromatography, crystallization, HPLC, etc., but are not limited thereto.

According to an embodiment of the present disclosure, a supernatant, obtained by centrifuging the culture at a low speed followed by removing the resulting biomass, was separated by ion exchange chromatography.

DETAILED DESCRIPTION OF THE INVENTION

Hereinafter, the present disclosure will be described in more detail with reference to the following Examples. However, these Examples are for illustrative purposes only, and the invention is not intended to be limited by these Examples.

EXAMPLE 1

Selection of Mutant Strains by Artificial Mutagenesis

To obtain a mutant microorganism strain having an enhanced ability to produce L-valine, the mutation of a microorganism was induced using the following method.

Specifically, a parental strain, L-valine-producing *Corynebacterium glutamicum Corynebacterium glutamicum* KCCM11201P (Korean Patent No. 10-1117022), was inoculated into a seed medium containing the components described below, which was sterilized at 121° C. for 15 minutes, cultured for 13 hours, and 25 mL of the culture medium was recovered. The recovered cultured medium was washed with 100 mM citrate buffer and N-methyl-N'-nitro-N-nitrosoguanidine (NTG) was added thereto at a final concentration of 400 μg/ml treated for 30 minutes, and the medium was washed with 100 mM phosphate buffer. The strains treated with NTG were spread on a minimal medium and the death rate was measured, and as a result, the death rate was shown to be 99.6%.

To obtain a mutant strain having resistance to α-aminobutyric acid (ABA), the NTG-treated strains were spread on a minimal medium containing ABA at a final concentration of 0 mM, 20 mM, 50 mM, 100 mM, and 200 mM, respectively. Then, the strains were cultured at 30° C. for 7 days to obtain an ABA-resistant mutant strain. The thus-obtained mutant strain was designated as *Corynebacterium glutamicum* NA100-311.

<Seed Medium>

Raw Sugar (20 g), Peptone (10 g), Yeast Extract (5 g), Urea (1.5 g), $KH_2PO_4$ (4 g), $K_2HPO_4$ (8 g), $MgSO_4.7H_2O$ (0.5 g), Biotin (100 μg), Thiamine HCl (1000 μg), Calcium-Pantothenic Acid (2000 μg), and Nicotinamide (2000 μg) (based on 1 L of distilled water), pH 7.0

<Minimal Medium>

Glucose (100 g), $(NH_4)_2SO_4$ (40 g), Soy Protein (2.5 g), Corn Steep Solids (5 g), Urea (3 g), $KH_2PO_4$ g), $MgSO_4.7H_2O$ (0.5 g), Biotin (100 μg), Thiamine HCl (1000 μg), Calcium-Pantothenic Acid (2000 μg), and Nicotinamide (3000 μg) (based on 1 L of distilled water), pH 7.0

EXAMPLE 2

Confirmation of the L-Valine-producing Ability of the Selected Strain and Confirmation of the Nucleotide Sequence of ilvN To confirm the L-valine-producing ability of *Corynebacterium glutamicum* NA100-311, the mutant strain selected in Example 1, the strain was cultured by the following method.

The parent strain (i.e., *Corynebacterium glutamicum* KCCM11201P) and the mutant strain *Corynebacterium glutamicum* N4100-311) were inoculated in an amount of a platinum loop into 250 mL corner baffle flasks containing 25 ml of the production medium described below and cultured at 30° C. for 72 hours with shaking at 200 rpm to produce L-valine.

<Production Medium>

Glucose (100 g), $(NH_4)_2SO_4$ (40 g), Soy Protein (2.5 g), Corn Steep Solids (5 g), Urea (3 g), $KH_2PO_4$ (1 g), $MgSO_4.7H_2O$ (0.5 g), Biotin (100 μg), Thiamine HCl (1000 μg), Calcium-Pantothenic Acid (2000 μg), and Nicotinamide (3000 μg) (based on 1 L of distilled water), pH 7.0

Upon completion of the cultivation, the amount of L-valine production was measured by high speed liquid chromatography. The concentrations of L-valine in the culture media of the experimental strains are shown in Table 1 below.

TABLE 1

| L-Valine productivity of ABA-resistant strains | | |
|---|---|---|
| Strain | L-Valine Concentration (g/L) | Optical Density (OD) |
| *Corynebacterium glutamicum* KCCM11201P | 2.8 | 47.5 |
| *Corynebacterium glutamicum* NA100-311 | 1.9 | 26.8 |

According to the results above, in the case of the parent strain *Corynebacterium glutamicum* KCCM11201P), the optical density of the culture was 47.5 and L-valine was produced in a concentration of 2.8 g/L, whereas, in the case of the mutant strain (i.e., *Corynebacterium glutamicum* NA100-311), L-valine was produced in a concentration of 1.9 g/L although the optical density of the culture was only 26.9. Upon calculation of the concentration of L-valine (g/L/OD) produced per optical density 1, the concentration of L-valine for the parent strain (Le., *Corynebacterium glutamicum* KCCM11201P) was shown to be 0.059 while the mutant strain (i.e., *Corynebacterium glutamicum*, NA100-311) showed an increased value of 0.071, thus suggesting that the amount of L-valine produced by the same amount of cells in the mutant strain was increased by 20.3% compared to that of the parent strain.

To confirm the nucleotide sequence of the ilvN gene, which encodes the small subunit of acetohydroxy acid synthase in the mutant strain (i.e., *Corynebacterium glutamicum* NA100-311), the chromosomal DNA of the mutant strain was amplified by polymerase chain reaction (hereinafter, PCR).

Specifically, first, an about 1726bp fragment was amplified using the chromosomal DNA of the mutant strain (i.e., *Corynebacterium glutamicum* NA100-311) as a template along with the primers of SEQ ID NOS: 1 and 2, under the following conditions: 28 cycles of denaturation at 94° C. for 1 min, annealing at 58° C. for 30 sec, and polymerization at 72° C. for 40 sec using Taq DNA polymerase. Upon analysis of the nucleotide sequence using the primers, it was confirmed that the 409$^{th}$ nucleotide, C, was substituted with T and this suggests that the mutation was the substitution of the 137$^{th}$ amino acid, leucine, with phenylalanine.

EXAMPLE 3

Preparation of a Vector Including a Substituted Nucleotide Sequence of ilvN

To prepare a vector including the mutated nucleotide sequence confirmed in Example 2, an about 1726bp fragment having BamHI and XbaI restriction sites was amplified using the chromosomal DNA of the mutant strain as a template along with the primers of SEQ ID NOS: 1 and 2, under the following conditions: 25 cycles of denaturation at 94° C. for 1 min, annealing at 58° C. for 30 sec, and polymerization at 72° C. for 1 min using Pfu DNA polymerase. The amplified fragment was treated with restriction enzymes, BamHI and XbaI, and ligated into a pDZ, which was treated with the same restriction enzymes, to prepare pDZ-ilvN(L137F).

EXAMPLE 4

Preparation of a Strain where a Nucleotide Sequence of ilvN is Substituted

To prepare a strain which includes the ilvN-mutated nucleotide sequence discovered in the above mutant strain, Corynebacterium glutamicum KCCM11201P, which produces L-valine, was used as the parent strain.

The Corynebacterium glutamicum KCCM11201P was transformed with the pDZ-ilvN(L137F) vector prepared in Example 3 by electroporation. An L-valine-producing strain, in which the 137$^{th}$ amino acid, leucine, was substituted with phenylalanine, in an amino acid sequence encoded by ilvN gene on the chromosome of Corynebacterium glutamicum KCCM11201P, was obtained by second crossover. The presence of the substitution of ilvN was confirmed by analyzing a 1726bp fragment with the primer of SEQ ID NO: 2, after amplifying the 1726bp fragment by PCR using the primers of SEQ ID NOS: 1 and 2 under the following conditions: 28cycles of denaturation at 94° C. for 1min, annealing at 58° C. for 30 sec, and polymerization at 72° C. for 40 sec using Taq DNA polymerase.

The strain transformed with the pDZ-ilvN(L137F) vector was named as Corynebacterium glutamicum KO-644 and deposited at the Korean Culture Center of Microorganisms (KCCM), which is recognized as an international depositary authority under the Budapest Treaty, on Nov. 22, 2013, under the accession number KCCM11485P.

EXAMPLE 5

Production of L-Valine in a Strain where a Nucleotide Sequence of ilvN is Substituted To produce L-valine from the Corynebacterium glutamicum KO-644, the L-valine-producing strain prepared in Example 4, the strain was cultured by the following method.

The parent strain (i.e., Corynebacterium glutamicum KCCM 11201P) and the Corynebacterium glutamicum KO-644 prepared above were inoculated in an amount of a platinum loop into 250 ml corner baffle flasks containing 25 mL of the production medium and cultured at 30° C. for 72 hours with shaking at 200 rpm to produce L-valine.

Upon completion of the cultivation, the amount of L-valine production was measured by high speed liquid chromatography. The concentrations of L-valine in the culture media of the experimental strains are shown in Table 2 below.

TABLE 2

L-Valine productivity of Corynebacterium glutamicum KCCM11201P and Corynebacterium glutamicum KCJ-644

| Strain | L-Valine Concentration (g/L) |
|---|---|
| Corynebacterium glutamicum KCCM11201P | 2.8 |
| Corynebacterium glutamicum KCJ-644 | 3.0 |

As shown in Table 2, the Cognebacterium glutamicum KO-644, which is an L-valine-producing strain having an L137F mutation on the ilvN gene, showed a 7.1% increase in L-valine productivity, compared to the parent strain, i.e., Corynebacterium glutamicum KCCM11201P.

EXAMPLE 6

Measurement of Acetohydroxy Acid Synthase Activity in a Strain where a Nucleotide Sequence of ilvN is Substituted To measure the acetohydroxy acid synthase activity in the Corynebacterium glutamicum KO-644, which is an L-valine-producing strain prepared in Example 4, an experiment was performed by the following method.

The parent strain (i.e., Corynebacterium glutamicum KCCM11201P) and the Corynebacterium glutamicum KCJ-644 prepared above were inoculated in an amount of a platinum loop into 250 mL corner baffle flasks containing 25 mL of the seed medium and cultured at 30° C. for 16 hours with shaking at 200 rpm. Upon completion of the cultivation, the culture medium was centrifuged and the supernatant was discarded, and the pellet was washed and mixed with a lysis buffer and the cells were pulverized with a bead homogenizer. The proteins present in the lysate were quantitated according to the Bradford assay, and the activity of acetohydroxy acid synthase was measured by measuring the acetoin produced when the lysate containing 100 μg/mL of proteins was used. The measurement results of the acetohydroxy acid synthase activity in each strain are shown in Table 3 below.

TABLE 3

| Strain | ilvN Activity (μM/mg/min) |
|---|---|
| Corynebacterium glutamicum KCCM11201P | 73.6 |
| Corynebacterium glutamicum KCJ-644 | 84.1 |

As shown in Table 3, the Corynebacterium glutamicum KCJ-644, which is an L-valine-producing strain having an L137F mutation on the ilvN gene, showed a 14.3% increase in L-valine productivity, compared to the parent strain, i.e., Corynebacterium glutamicum KCCM11201P.

From the foregoing, a skilled person in the art to which the present disclosure pertains will be able to understand that the present disclosure may be embodied in other specific forms without modifying the technical concepts or essential characteristics of the present disclosure. In this regard, the exemplary embodiments disclosed herein are only for illustrative purposes and should not be construed as limiting the scope of the present disclosure. On the contrary, the present disclosure is intended to cover not only the exemplary embodiments but also various alternatives, modifications, equivalents, and other embodiments that may be included within the spirit and scope of the present disclosure as defined by the appended claims.

The invention claimed is:

1. An acetohydroxy acid synthase variant, wherein the 137$^{th}$ amino acid from the N-terminus of an amino acid sequence of SEQ ID NO: 3, leucine (L), is substituted with an amino acid other than leucine, and thereby releasing the feedback inhibition to L-valine.

2. The acetohydroxy acid synthase variant of claim 1, wherein the variant has the amino acid sequence of SEQ ID NO: 4.

* * * * *

SEQUENCE LISTING

<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
cgttggccag caccagatgt                                              20

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
gatgtcgtca gctggcttga tc                                           22

<210> SEQ ID NO 3
<211> LENGTH: 172
<212> TYPE: PRT
<213> ORGANISM: Corynebacterium glutamicum
<220> FEATURE:
<221> NAME/KEY: PEPTIDE
<222> LOCATION: (1)...(172)
<223> OTHER INFORMATION: Acetohydroxy acid synthase

<400> SEQUENCE: 3

Met Ala Asn Ser Asp Val Thr Arg His Ile Leu Ser Val Leu Val Gln
1               5                   10                  15

Asp Val Asp Gly Ile Ile Ser Arg Val Ser Gly Met Phe Thr Arg Arg
            20                  25                  30

Ala Phe Asn Leu Val Ser Leu Val Ser Val Lys Thr Glu Thr Leu Gly
        35                  40                  45

Ile Asn Arg Ile Thr Val Val Asp Ala Asp Glu Leu Asn Ile Glu
    50                  55                  60

Gln Ile Thr Lys Gln Leu Asn Lys Leu Ile Pro Val Leu Lys Val Val
65                  70                  75                  80

Arg Leu Asp Glu Glu Thr Thr Ile Ala Arg Ala Ile Met Leu Val Lys
                85                  90                  95

Val Ser Ala Asp Ser Thr Asn Arg Pro Gln Ile Val Asp Ala Ala Asn
            100                 105                 110

Ile Phe Arg Ala Arg Val Val Asp Val Ala Pro Asp Ser Val Val Ile
        115                 120                 125

Glu Ser Thr Gly Thr Pro Gly Lys Leu Arg Ala Leu Leu Asp Val Met
130                 135                 140

Glu Pro Phe Gly Ile Arg Glu Leu Ile Gln Ser Gly Gln Ile Ala Leu
145                 150                 155                 160

Asn Arg Gly Pro Lys Thr Met Ala Pro Ala Lys Ile
                165                 170

<210> SEQ ID NO 4
<211> LENGTH: 172
<212> TYPE: PRT
<213> ORGANISM: Artificial Sequence
<220> FEATURE:
<223> OTHER INFORMATION: acetohydroxy acid synthase variant

```
<400> SEQUENCE: 4

Met Ala Asn Ser Asp Val Thr Arg His Ile Leu Ser Val Leu Val Gln
1               5                   10                  15

Asp Val Asp Gly Ile Ile Ser Arg Val Ser Gly Met Phe Thr Arg Arg
                20                  25                  30

Ala Phe Asn Leu Val Ser Leu Val Ser Val Lys Thr Glu Thr Leu Gly
            35                  40                  45

Ile Asn Arg Ile Thr Val Val Val Asp Ala Asp Glu Leu Asn Ile Glu
    50                  55                  60

Gln Ile Thr Lys Gln Leu Asn Lys Leu Ile Pro Val Leu Lys Val Val
65                  70                  75                  80

Arg Leu Asp Glu Glu Thr Thr Ile Ala Arg Ala Ile Met Leu Val Lys
                85                  90                  95

Val Ser Ala Asp Ser Thr Asn Arg Pro Gln Ile Val Asp Ala Ala Asn
                100                 105                 110

Ile Phe Arg Ala Arg Val Val Asp Val Ala Pro Asp Ser Val Val Ile
            115                 120                 125

Glu Ser Thr Gly Thr Pro Gly Lys Phe Arg Ala Leu Leu Asp Val Met
    130                 135                 140

Glu Pro Phe Gly Ile Arg Glu Leu Ile Gln Ser Gly Gln Ile Ala Leu
145                 150                 155                 160

Asn Arg Gly Pro Lys Thr Met Ala Pro Ala Lys Ile
                165                 170

<210> SEQ ID NO 5
<211> LENGTH: 519
<212> TYPE: DNA
<213> ORGANISM: Artificial Sequence
<220> FEATURE:
<223> OTHER INFORMATION: acetohydroxy acid synthase variant

<400> SEQUENCE: 5
atggctaatt ctgacgtcac ccgccacatc ctgtccgtac tcgttcagga cgtagacgga    60
atcatttccc gcgtatcagg tatgttcacc cgacgcgcat tcaacctcgt gtccctcgtg   120
tctgtaaaga ccgaaacact cggcatcaac cgcatcacgg ttgttgtcga cgccgacgag   180
ctcaacattg agcagatcac caagcagctc aacaagctga tccccgtgct caaagtcgtg   240
cgacttgatg aagagaccac catcgcccgc gcaatcatgc tggttaaggt ctctgcggat   300
agcaccaacc gtccgcagat cgtcgacgcc gcgaacatct ccgcgcccg agtcgtcgac   360 gtggctccag actctgtggt tattgaatcc acaggcaccc caggcaagtt ccgcgcactg   420
cttgatgtga tggaaccatt cggaatccgc gaactgatcc aatccggaca gattgcactc   480
aaccgcggtc cgaagaccat ggctccggcc aagatctaa                          519
```